United States Patent [19]

Garland

[11] Patent Number: 4,611,065

[45] Date of Patent: Sep. 9, 1986

[54] METHOD FOR PREPARING 5-FLUOROPROSTACYCLINS

[75] Inventor: Robert B. Garland, Northbrook, Ill.

[73] Assignee: G. D. Searle & Co., Skokie, Ill.

[21] Appl. No.: 695,146

[22] Filed: Jan. 25, 1985

[51] Int. Cl.$^4$ ........................................ C07D 307/935
[52] U.S. Cl. .................................... 549/214; 549/465
[58] Field of Search .............................. 549/465, 214

[56] References Cited

U.S. PATENT DOCUMENTS

| | | | |
|---|---|---|---|
| 4,324,730 | 4/1982 | Fried | 549/465 |
| 4,472,428 | 9/1984 | Toru et al. | 549/465 |
| 4,540,801 | 9/1985 | Nysted et al. | 549/465 |

FOREIGN PATENT DOCUMENTS 062303 10/1982 European Pat. Off. .

OTHER PUBLICATIONS

R. A. Johnson, et al., "Synthesis and Stereochemistry of Prostacyclin and Synthesis of 6-Ketoprostaglandin F$_{1\alpha}$", *J. Am. Chem. Soc.*, 99, 4182–4184 (1977).
R. A. Johnson, et al., "The Chemical Structure of Prostaglandin X (Prostacyclin)," *Prostaglandins*, 12, 915–928 (1976).
C. Pace-Asciak and L. S. Wolfe, "A Novel Prostaglandin Derivative Formed from Arochidonic Acid by Rat Stomach Homogenates", *Biochemistry*, 10, 3657–3664 (1971).
W. E. Barnette, "The Synthesis and Biology of Fluorinated Prostacyclins," *CRC Critical Reviews of Biochemistry*, 15, 201–235 (1984).
B. Loev and M. M. Goodman, "Dry-Column Chromatography . . . ", *Chemistry and Industry*, 2026–2032 (1967).
R. A. Johnson, et al., "Synthesis and Characterization of Prostacyclin, 6-Ketoprostaglandin F$_{1\alpha}$, Prostaglandin I$_1$, and Prostaglandin I$_3$," *J. Am. Chem. Soc.*, 100, 7690–7704 (1978).
N. Whittaker, "A Synthesis of Prostacyclin Sodium Salt," *Tetrahedron Lett.*, 2805–2808 (1977).

*Primary Examiner*—Henry R. Jiles
*Assistant Examiner*—Bernard I. Dentz
*Attorney, Agent, or Firm*—Stuart L. Melton; R. E. L. Henderson

[57] ABSTRACT

This invention relates to a process for preparing 5-fluoroprostacyclins that are useful for the treatment of platelet dysfunction.

9 Claims, No Drawings

METHOD FOR PREPARING 5-FLUOROPROSTACYCLINS

BACKGROUND OF THE INVENTION (a) Field of the Invention

This invention relates to a process for preparing 5-fluoroprostacyclins that are useful for the treatment of platelet dysfunction. More particularly, this invention relates to a process for preparing 5-fluoroprostacycylins.

The prototypical prostacyclin, an organic compound related to prostaglandins, is (5Z)-9-deoxy-6,9α-epoxy-$\Delta^5$-PGF$_{1\alpha}$. See, for example, R. A. Johnson et al, *J. Am. Chem. Soc.*, 99, 4182 (1977); R. A. Johnson et al., *Prostaglandins*, 12, 915 (1976); C. Pace-Asciak and L. S. Wolfe, *Biochemistry*, 10, 3657 (1971). Other related cyclic prostaglandins are generally collectively referred to as "prostacyclins." Prostaglandins and prostacyclins elicit a number of biological responses and typically are very potent in doing so. Among these biological effects are inhibition of blood platelet aggregation; stimulation of smooth muscle; inhibition of gastric secretion; cytoprotection of the gastric mucosa; and reduction of gastrointestinal effects of systemic administration of prostaglandin synthetase inhibitors.

(b) Prior Art

Methods for preparing various fluorinated prostacyclins are extensively reviewed by William E. Barnette in "The Synthesis and Biology of Fluorinated Prostacyclins," *CRC Critical Reviews in Biochemistry*, 15, 201–235 (1984). The method described in this invention is not, however, disclosed in the review. U.S. Pat. No. 4,324,730 discloses 6,9α-epoxy-5-fluoro-11α,15S-dihydroxyprosta-5E,13E-dien-1-oic acid (compare Formulas XVI and XVII of Scheme E, below), but does not describe the properties of the compound nor a specific operative method of preparation.

European Patent Application (Publication No. 062303, Oct. 13, 1982), assigned to the assignee of this invention, discloses 5-fluoroprostacyclins, including 5,6- or 6,7-unsaturated derivatives of the formulas

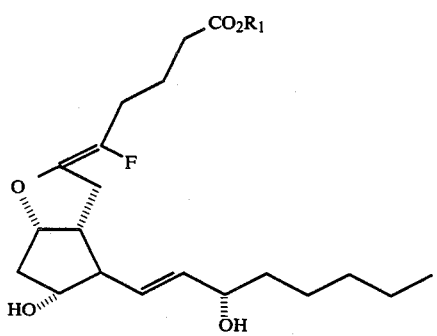

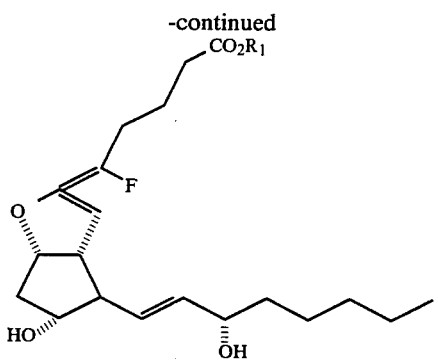

A process for their preparation is disclosed utilizing the reaction of PGI$_2$ methyl ester starting material with a fluorinating agent, preferably perchloryl fluoride, in a protic solvent, such as methanol. The resultant 5-fluoro-6-methoxy-PGI$_1$ methyl ester represents a previously unknown key intermediate from which the valuable $\Delta^5$-5-fluoro- and $\Delta^{6,7}$-5-fluoroprostacyclins described are prepared. The foregoing published application does not specifically disclose the sterochemistry of the 5-position fluoro group nor methods for obtaining individual isomers.

SUMMARY OF THE INVENTION

Applicants have now discovered an advantageous stereospecific process for preparing and separating 5-fluoro-6-methoxy PGI$_1$ intermediates into their component diasteromers and employing the component diastereomers to obtain the desired individual final products with improved overall yield and purity. More specifically, this invention relates to a process for preparing 5-fluoroprostacyclins by which silylated prostaglandin F$_{2\alpha}$ esters are fluorinated; the resultant 5-fluoro intermediates are separated into individual isomers; the isomers are subjected to conditions that introduce a 5,6- or 6,7-double bond; and the resultant compounds are separated into component 5-fluoroprostacyclin esters of this invention. Additionally, the esters may further be saponified to produce corresponding 5-fluoroprostacylin salts of this invention.

DESCRIPTION OF THE INVENTION

The method of this invention is described by the following Schemes. Silyl protecting groups in the Schemes are designated by $R^2$ and $R^3$, which represent hydrocarbon-substituted silicon atoms. Preferred silyl protecting groups include triethylsilyl and t-butyldiphenylsilyl groups. The initial fluorination of silylated prostaglandin F$_{2\alpha}$ esters is illustrated by Scheme A.

SCHEME A

Silylated prostaglandin F$_{2\alpha}$ esters of Formula I are fluorinated to form a mixture of 5-fluoro-6-methoxy isomers, denoted by Formula II. Preferred esters include compounds in which R$^1$ is a lower alkyl group of 1 to 6 carbon atoms, inclusive, such as methyl, ethyl, propyl, butyl, pentyl, hexyl, and the isomeric forms thereof. Although fluorination may be effected with fluorine gas or other fluorinating agents in an alcohol, preferred fluorinating conditions employ perchloryl fluoride in a protic solvent such as methanol containing a base such as potassium carbonate or the more methanol soluble cesium carbonate. When using cesium carbonate, the temperatures may be somewhat lower than for potassium carbonate—for example 15° rather than 25° to 35°—and undesired byproducts are reduced. The mixture of isomers can then be resolved into individual components, Formulas III through IV, by chromatography. The preferred chromatographic system depends somewhat on the silyl protecting group. Initial separations are preferably performed using silica gel eluted with mixtures of ethyl acetate/hexane, the exact proportion tailored to each compound type being separated. For triethylsilyl-protected isomers, preferred further chromatographic separation employs a sequence of columns: (1) Florisil ® (Trademark of Floridin

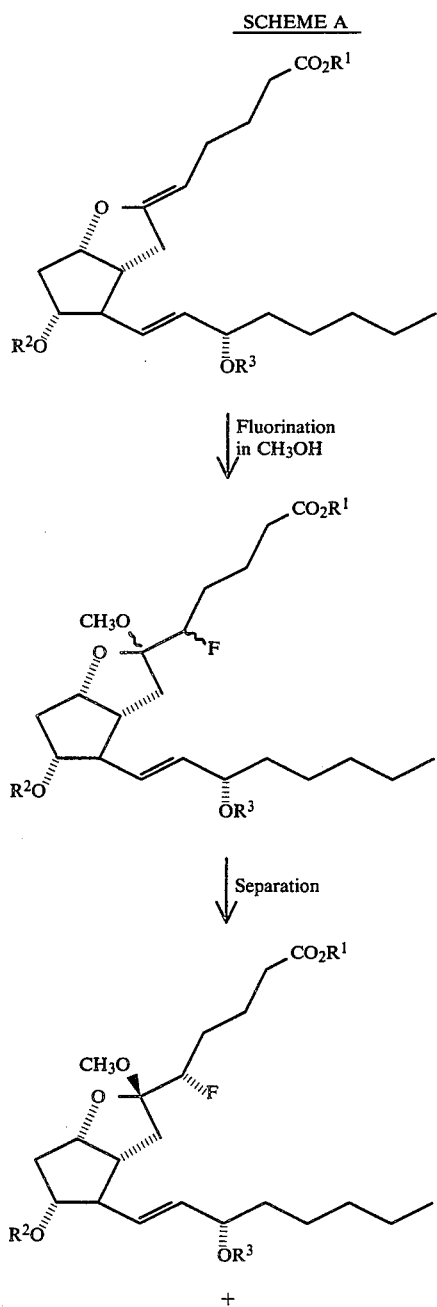

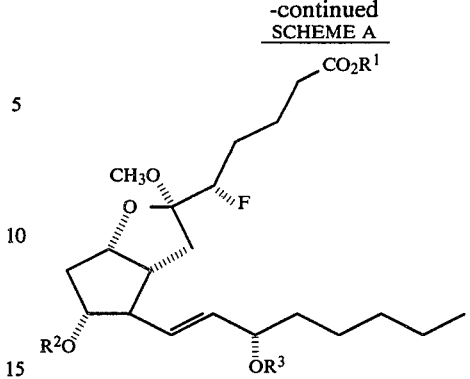

Company, Warren, PA) activated magnesium silicate gel eluted with hexane containing a few percent (for example, about 1 to 10% by volume) of ethyl acetate and small quantities (for example, about 0.1 to 1.0% by volume) of triethylamine cleanly separates some isomers, after which (2) Partisil ® (Trademark of Whatman Chemical Separations, Inc., Clifton, NJ 07014) silica gel eluted with about 97:3 (by volume) 1,1,2-trichlorotrifluoroethane/ethyl acetate cleanly separates the rest.

All the individual triethylsilyl protected isomers are easily resolved using the above chromatography system. Although the corresponding t-butyldiphenylsilyl protected isomers are generally less easily resolved, the t-butyldiphenylsilyl protected 5S-fluoro isomer of Formula III is more readily resolved during chromatography than is the corresponding 5S-fluoro isomer of Formula IV. Furthermore, the enhanced stability of the t-butyldiphenylsilyl protecting group (relative to the triethylsilyl group) allows a convenient recycling method to be used. Impure chromatographic fractions containing isomer IV can be equilibrated to form additional isomer III by treating with a mild acid, such as camphorsulfonic acid, in methanol. Repeating the chromatography described above allows isolation of the more easily resolved isomer III.

Scheme B illustrates the preparation of the 5S-fluoro-6,13E-diene prostacyclins of this invention from the 5S-fluoro compounds of Formulas III and IV, either individually or as a mixture, using the method of this invention.

SCHEME B

The 5S-fluoro compounds, represented collectively in Scheme B by Formula VII, are converted to 5S-fluoro-6,13E-dienes of Formula VIII by elimination of methanol. Preferred elimination conditions include heating xylene solutions of compounds of Formula VII with magnesium triflate in the presence of traces of picoline. Partition between water and an organic solvent, such as hexane or another hydrocarbon, removes water-soluble impurities. The 5S-fluoro-6,13E-dienes of Formula VIII, which are soluble in the organic phase, are purified by chromatography using silica gel columns. Preferred eluents include hexane containing a few percent (for example, about 1 to 10% by volume) of ethyl acetate and small quantities (for example, about 0.1 to 1.0% by volume) of triethylamine. Silyl protecting groups are removed by methods known in the art. A preferred method employs a slight molar excess of tetrabutylammonium fluoride in tetrahydrofuran at room temperature. Under these conditions, less hindered silyl protecting groups are removed quickly (about fifteen minutes for the triethylsilyl group), whereas more hindered silyl protecting groups are removed more slowly (about twenty hours for the t-butyldiphenylsilyl group). Chromatography affords pure prostacyclin esters of Formula IX. A preferred chromatographic method is so-called "dry-column" liquid

SCHEME B

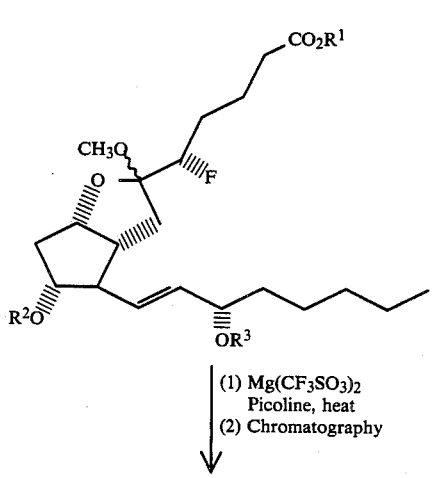

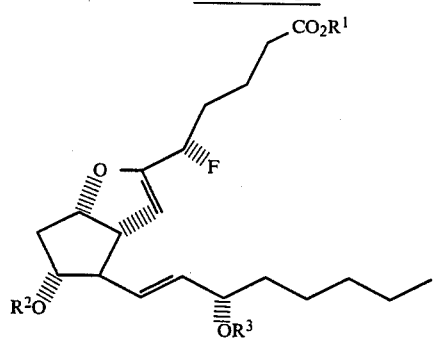

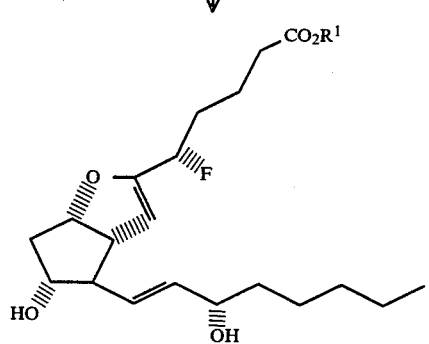

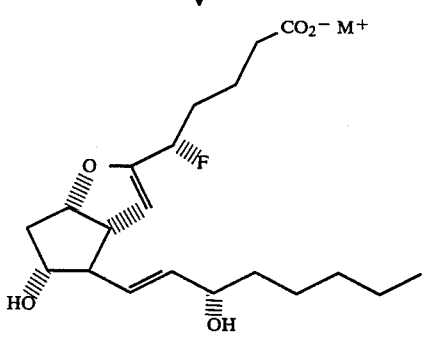

chromatography, in which concentrated sample solutions are placed on a dry silica gel column and then eluted. A preferred elution scheme uses (1) about equal volumes of hexane and ethyl acetate, plus about 1% by volume of triethylamine, to remove non-polar impurities, and then (2) ethyl acetate containing a few percent (about 1 to 3% by volume) of triethylamine.

The prostacyclin esters of Formula IX may be saponified to form salts of Formula X, in which $M^+$ represents an alkali metal ion (lithium, sodium, potassium, or cesium). A preferred saponification method employs a 5% molar excess of sodium hydroxide in methanol-water at room temperature. After concentration, the resultant salts are freeze-dried.

Scheme C illustrates the same elimination reaction described above for Scheme B, but using the 5R-fluoro compounds of Formulas V and VI, represented collectively in Scheme C by Formula IX, instead of the 5S-fluoro compounds.

SCHEME C

The elimination of methanol from compound IX is performed in the same manner as described in Scheme B, but the elimination forms both the 5R-fluoro-6,13E-diene of Formula XII and 5-fluoro-5E,13E-diene of Formula XIII. The compounds can be separated by the chromatographic method described above for Scheme B. The enhanced stability of the t-butyldiphenylsilyl protecting group (relative to the triethylsilyl group) again

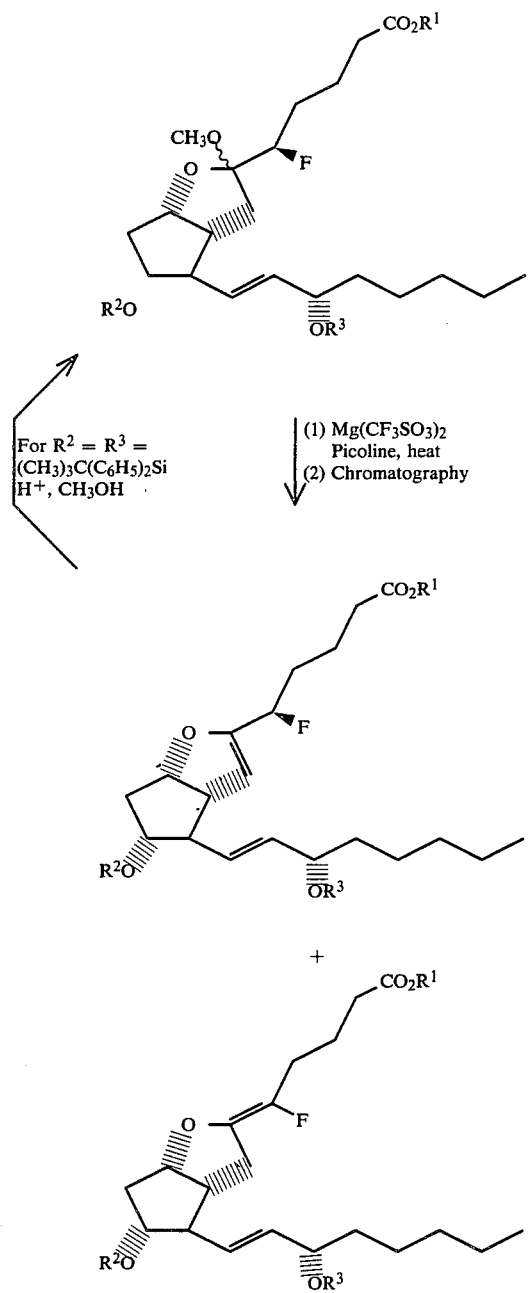

allows a convenient recycling method to be used. The 5R-fluoro-6,13E-diene of Formula XII can be converted to the original mixture represented by Formula XI by treating with a mild acid, such as camphorsulfonic acid, in methanol. Repeating the elimination of methanol and the chromatography described above allows isolation of additional 5-fluoro-5E,13E-diene of Formula XIII.

Scheme D illustrates the preparation of the 5R-fluoro-6,13E-diene prostacyclins of this invention from the 5R-fluoro compounds of Formula XII.

SCHEME D

Compounds of Formula XIV are prepared by removing silyl protecting groups from compounds of Formula XII by the same method described above for Scheme B. Saponification of compounds XIV by the same method described for Scheme B affords the salts of Formula XV, in which $M^+$ represents an alkali metal ion (lithium, sodium, potassium, or cesium).

Scheme E illustrates the preparation of the 5-fluoro-5E,13E-diene prostacyclins of this invention from the compounds of Formula XIII.

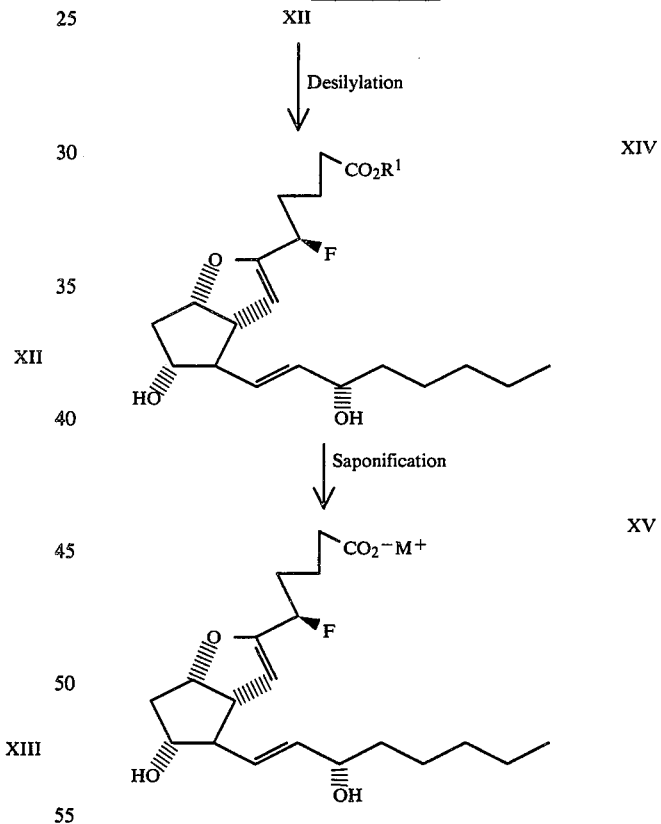

SCHEME E

Compounds of Formula XVI are prepared by removing silyl protecting groups from compounds of Formula XIII by the same method described above for Scheme B. Saponification of compounds XVI by the same method described for Scheme B affords the salts of Formula XVII, in which $M^+$ represents an alkali metal ion (lithium, sodium, potassium, or cesium).

By virtue of the activity against platelet aggregation, the compounds of this invention are useful in treating thrombotic disorders in mammals.

The following examples further illustrate details for the process of this invention. The invention, which is set forth in the foregoing disclosure, is not to be construed or limited either in spirit or in scope by these examples. Those skilled in the art will readily recognize that known variations of the conditions may be used in the following preparative procedures. All temperatures are degrees Celsius unless otherwise noted.

CHROMATOGRAPHIC PROCEDURES

Procedure 1 Medium-Pressure Liquid Chromatography

Except as otherwise specified in the following Examples, separations using medium-pressure liquid chromatography (MPLC) were performed using silica gel (manufactured by Woelm Pharma

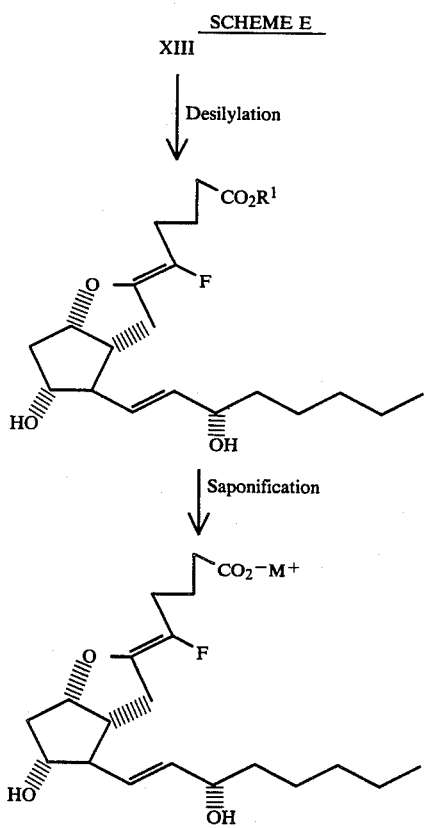

SCHEME E

GmbH, Eschwege, West Germany, and available in the United States from Universal Scientific Incorporated, Atlanta, GA 30341) packed in a column measuring 25 mm in diameter and 1 m in length. The silica gel was prewashed with 95:5 (by volume) ethyl acetate/triethylamine and then with the eluent indicated in each Example. Eluents were ethyl acetate/hexane mixtures containing about 0.2% by volume of triethylamine. When step gradient elution was used for chromatographic separations, relative volumes of ethyl acetate and hexane for each step are indicated. Upon completion of each separation, the column was regenerated by washing with ethyl acetate followed by ethyl acetate saturated with water.

Procedure 2 Dry-Column Liquid Chromatography

Dry-column liquid chromatography, in which samples are first placed on a solvent-free chromatography column and then eluted by adding solvent, was carried out using a modification of the method of Loev. See B. Loev and M. M. Goodman, *Chemistry and Industry*, 2026 (1967). Chromatographic grade silica gel (manufactured by Woelm Pharma GmbH, Eschwege, West Germany, and available in the United States from Universal Scientific Incorporated, Atlanta, GA 30341) deactivated by about 8% by weight of water was pretreated with 10 ml of ethyl acetate and 1 ml of triethylamine for every 100 g of absorbent, and then packed in a column measuring about 20 mm in diameter and about 25 cm in length. After samples to be purified were placed on the column, the columns were eluted initially with 50:49:1 (by volume) hexane/ethyl acetate/triethylamine to remove less polar components. Elution was then continued with 99:1 (by volume) ethyl acetate/triethylamine until purified title compounds were collected, as indicated by thin-layer chromatography.

Procedure 3 Thin-Layer Chromatography

Chromatography procedures were monitored by thin-layer chromatography (tlc) using 20-cm Polygram (Trademark of Machery-Nagel, West Germany) SIL G/UV$_{254}$ plastic plates, available from Sybron-Brinkman and distributed by Brinkmann Instruments Co., Westbury, NY 11590. The plates were developed using 9:1 hexane/ethyl acetate for silylated product mixtures and with ethyl acetate for product mixtures from which silyl groups had been removed. Individual isomers were best resolved by multiple development (3 to 6 times). Data are reported as $R_f$ values, the ratio of the distance moved by the compounds to the distance moved by the solvent front.

DESCRIPTION OF THE METHODS

EXAMPLE 1

Methyl 11α,15S-bis[(triethylsilyl)oxy]-6,9α-epoxyprosta-5Z,13E-dien-1-oate

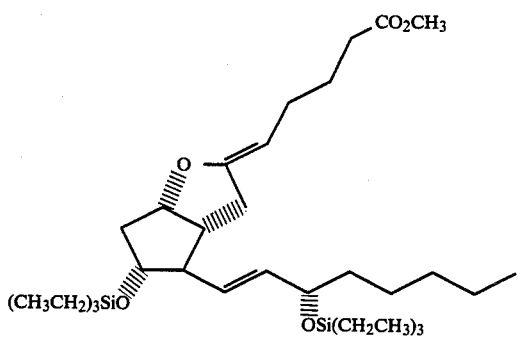

To a stirred solution of 5.1 g of the methyl ester of prostaglandin F$_{2α}$ in 25 ml of chilled (ca. 0°) dichloromethane was added 12.5 g of sodium bicarbonate and 40 ml of water. After thirty minutes a solution of 3.9 g of iodine in 125 ml of dichloromethane was added slowly over about one hour. After additional stirring for one hour in the dark, the reaction was quenched with 25 ml of 5% aqueous sodium sulfite and the mixture diluted with 100 ml of water. The resultant aqueous layer was separated and extracted twice more with 100 ml of dichloromethane. The organic layers were combined and washed with water, dried over sodium sulfate, filtered, and concentrated in vacuo. The residue was chromatographed by the method of Procedure 1 using gradient elution with 60 to 80% (by volume) of ethyl acetate, giving 6.6 g of an isomeric mixture of 5-iodoprostacyclins. See R. A. Johnson, F. H. Lincoln, E. G. Nidy, W. P. Schneider, J. L. Thompson, U. Axen, *J. Am. Chem. Soc.*, 100, 7690–7704 (1978). The isomeric mixture was dissolved in 65 ml of dimethylformamide containing 5.4 g of imidazole. The solution was cooled to ca. 0° and chlorotriethylsilane (5.2 ml) was added over a five-minute period. The mixture was allowed to warm to room temperature and was stirred for two hours. After again cooling to 0°, the mixture was diluted with 200 ml each of hexane and water. After the aqueous layer was separated and extracted with hexane, the combined organic layers were washed with four portions of water and then with brine, dried over sodium sulfate, filtered, and concentrated in vacuo. The residue was chromatographed by the method of Procedure 1 using 5% (by volume) ethyl acetate, giving 8.2 g of the triethylsilylated isomeric mixture of 5-iodoprostacyclins. The triethylsilylated mixture was dissolved in 50 ml of toluene and added to a solution of 1,8-diazabicyclo[5.4.0]undec-7-ene (DBU) in 350 ml of toluene. About 50 ml of solvent was removed by distillation (to assure dryness) and the remaining solution was heated at reflux for eighteen hours. The mixture was cooled to room temperature and filtered. The filtrate was washed with three portions of 2% aqueous sodium carbonate, dried over sodium sulfate, filtered, and concentrated in vacuo. The residue was chromatographed on Florisil ® (Trademark of Floridin Company, Warren, PA) activated magnesium silicate gel packed in a column measuring 25 mm in diameter and 1 m in length (and prewashed with 95:5 by volume of ethyl acetate/triethylamine before washing with the eluent used for the separation) using 98.5:1:0.5 (by volume) hexane/ethyl acetate/triethylamine as eluent. The title compound (6.3 g) was eluted in early fractions. For the dehydroiodination using DBU, see the methods of (1) R. A. Johnson et al., *J. Am. Chem. Soc.*, 100, 7690–7704 (1978) and (2) N. Whittaker, *Tetrahedron Lett.*, 2805–2808 (1977).

$^{13}$C nmr (CDCl$_3$ containing trace of C$_5$D$_5$N): δ(ppm) 51.3 (1-OCH$_3$); 174.5 (1-C); 33.7 (2-C); 24.9 (3-C); 25.6 (4-C); 95.6 (5-C); 155.1 (6-C); 33.4 (7-C); 44.7 (8-C); 83.6 (9-C); 42.2 (10-C); 77.9 (11-C); 53.9 (12-C); 129.5 (13-C); 135.6 (14-C); 73.2 (15-C); 38.8 (16-C); 25.2 (17-C); 32.0 (18-C); 22.8 (19-C); 14.1 (20-C); 5.0 and 5.1 (SiCH$_2$'s); 6.9 (ethyl CH$_3$'s) tlc: R$_f$ 0.36.

EXAMPLE 2

Methyl 11α,15S-bits[(triethylsilyl)oxy]-6,9α-epoxy-5S-fluoro-6S-methoxyprost-13E-en-1-oate

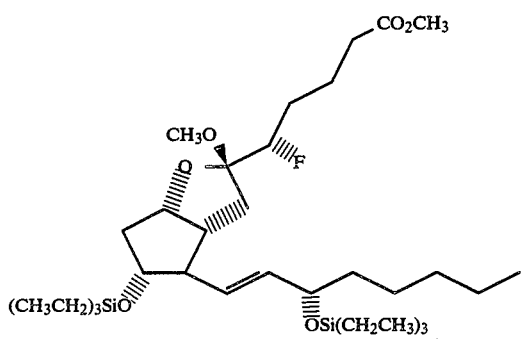

To a mixture of 1.64 g of the title product of Example 1 and 2.20 g of potassium carbonate in 40 ml of methanol, stirred at 15° under nitrogen, was added 1.0 ml of perchloryl fluoride over a thirty-minute period. The mixture was allowed to warm to room temperature while stirring an additional thirty minutes. After being diluted with 200 ml of ice water, the mixture was extracted with hexane. The organic layer was washed successively with water and brine, dried over sodium sulfate, filtered, and concentrated in vacuo. The residue was chromatographed by the method of Procedure 1 using 3% (by volume) of ethyl acetate, giving two major fractions. The slower fraction was concentrated in vacuo to give 460 mg of the title compound.

nmr (CDCl$_3$ containing trace of C$_5$D$_5$N) Proton: δ (ppm) 3.22 (s, 3H, 6-OCH$_3$) 13$_C$: δ (ppm) 29.9 (J$_{CCF}$=21 Hz, 4-C); 91.7 (J$_{CF}$=179 HZ, 5-C); 110.9 (J$_{CCF}$=23 Hz, 6-C); 37.1 (7-C); 45.0 (8-C); 81.7 (9-C) tlc: R$_f$ 0.18.

EXAMPLE 3

Methyl 11α,15S-bis[(triethylsilyl)oxy]-6,9α-epoxy-5S-fluoro-6R-methoxyprost-13E-en-1-oate

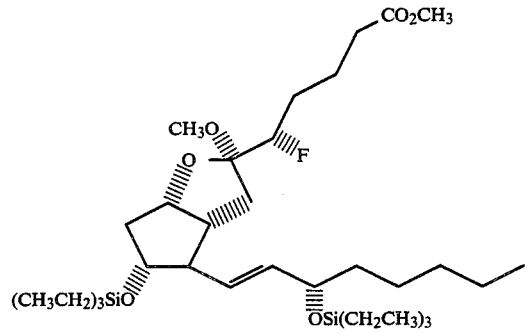

The faster chromatography fraction of Example 2 was further chromatographed on Florisil ® (Trademark of Floridin Company, Warren, PA) activated magnesium silicate gel packed in a column measuring 25 mm in diameter and 1 m in length using 97:2.5.:0.5 (by volume) hexane/ethyl acetate/triethylamine as eluent. Again, two major fractions were isolated. The slower fraction was concentrated in vacuo to give 150 mg of the title compound.

nmr (CDCl$_3$ containing trace of C$_5$D$_5$N) Proton: δ (ppm) 3.37 (s, 3H, 6-OCH$_3$) 13$_C$: δ (ppm) 29.9 (J$_{CCF}$=21 Hz, 4-C); 94.9 (J$_{CF}$=177 Hz, 5-C); 110.0 (J$_{CCF}$=24 Hz, 6-C); 35.9 (7-C); 45.2 (8-C); 82.4 (9-C) tlc: R$_f$ 0.28.

EXAMPLE 4

Methyl 11α,15S-bis[(triethylsilyl)oxy]-6,9α-epoxy-5R-fluoro-6S-methoxyprost-13E-en-1-oate

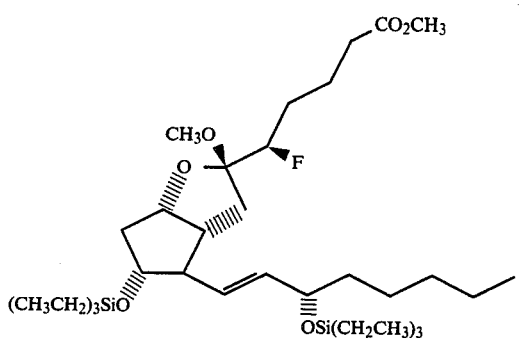

The faster chromatography fraction of Example 3 was further purified by high performance liquid chromatography on a Partisil ® (Trademark of Whatman Chemical Separations, Inc., Clifton, NJ 07014) silica gel packed in a column measuring 9.4 mm in diameter and 500 mm in length using 97:3 (by volume) 1,1,2-trichlorotrifluoroethane/ethyl acetate as eluent. Again, two major fractions were isolated. The faster fraction was concentrated in vacuo to give 820 mg of the title compound.

nmr (CDCl$_3$ containing trace of C$_5$D$_5$N) Proton: δ (ppm) 3.29 (s, 3H, 6-OCH$_3$) $^{13}$C: δ (ppm) 29.9 ($J_{CCF}$)=21 Hz, 4-C); 93.1 ($J_{CF}$=177 Hz, 5-C); 110.4 ($J_{CCF}$=22 Hz, 6-C); 39.2 (7-C); 45.3 (8-C); 82.5 (9-C) tlc: R$_f$0.25.

EXAMPLE 5

Methyl 11α,15S-bis[(triethylsilyl)oxy]-6,9α-epoxy-5R-fluoro-6R-methoxyprost-13E-en-1-oate

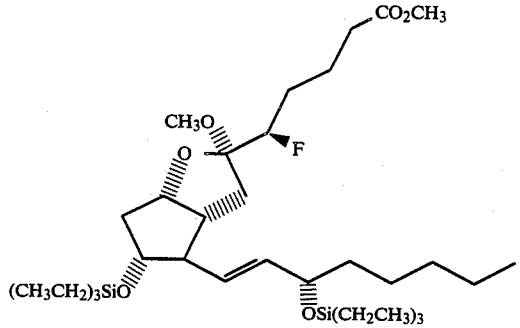

The slower chromatography fraction of Example 4 was concentrated in vacuo to give 265 mg of the title compound. nmr (CDCl$_3$ containing trace of C$_5$D$_5$N) Proton: δ (ppm) 3.30 (s, 3H, 6-OCH$_3$) $^{13}$C: δ (ppm) 29.8 ($J_{CCF}$=21 Hz, 4-C); 92.3 ($J_{CF}$=179 Hz, 5-C); 111.2 ($J_{CCF}$=22 Hz, 6-C); 34.2 (7-C); 45.2 (8-C); 82.4 (9-C) tlc: R$_f$0.25.

EXAMPLE 6

Methyl 11α,15S-bis[(triethylsilyl)oxy]-6,9α-epoxy-5-fluoroprosta-5E,13E-dien-1-oate, Method A

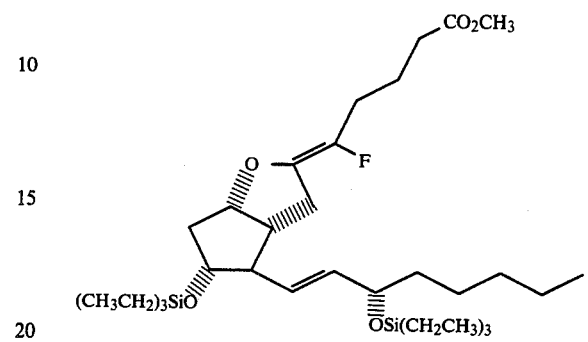

To a solution of 358 g of the title product of Example 4 in 10 ml of xylene was added 2 drops of 2-picoline and 5 mg of magnesium triflate. The mixture was stirred at reflux under nitrogen for two hours. After cooling and filtering the mixture, the filtrate was concentrated under a nitrogen stream and chromatographed by the method of Procedure 1 using 2% (by volume) of ethyl acetate, giving two major fractions. The faster fraction was concentrated in vacuo to give 22 mg of the title compound.

$^{13}$C nmr (CDCl$_3$ containing trace of C$_5$D$_5$N): δ (ppm) 26.9 ($J_{CCF}$=25 Hz, 4-C); 142.8 ($J_{CF}$=222 Hz, 5-C); 141.9 ($J_{CCF}$=48 Hz, 6-C); 29.7 (7-C); 44.8 (8-C); 84.0 (9-C) tlc: R$_f$0.35.

EXAMPLE 7

Methyl 11α,15S-bis[(triethylsilyl)oxy]-6,9α-epoxy-5R-fluoroprosta-6,13E-dien-1-oate, Method A

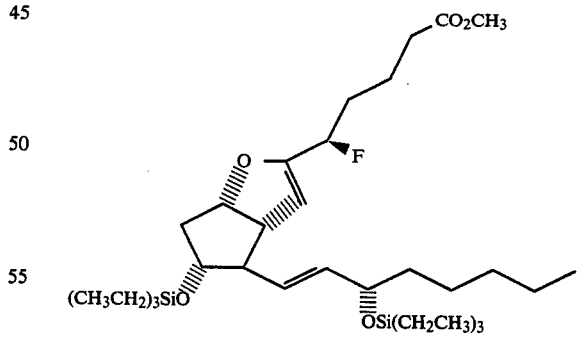

The slower chromatography fraction of Example 6 was concentrated in vacuo to give 232 mg of the title compound.

$^{13}$nmr (CDCl$_3$ containing trace of C$_5$D$_5$N): δ (ppm) 20.5 ($J_{CCCF}$=4 Hz, 3-C); 32.1 ($J_{CCF}$=22 Hz, 4-C); 87.7 ($J_{CF}$=169 Hz, 5-C); 154.3 ($J_{CCF}$=22 Hz, 6-C); 101.7 ($J_{CCCF}$=6 Hz, 7-C); 50.6 (8-C); 83.7 (9-C) tlc: R$_f$0.34. Unreacted title product of Example 4 was recovered in later fractions.

EXAMPLE 8

Methyl 11α,15S-bis[(triethylsilyl)oxy]-6,9α-epoxy-5-fluoro-prosta-5E,13E-dien-1-oate, Method B The title compound (12 mg) was prepared by the method of Example 6, except that the title product of Example 5 (185 mg) was used instead of the title product of Example 4 and the mixture was heated at reflux for eighteen hours. The title compound was identical to that of Example 6.

EXAMPLE 9

Methyl 11α,15S-bis[(triethylsilyl)oxy]-6,9α-epoxy-5R-fluoro-prosta-6,13E-dien-1-oate, Method B The slower chromatography fraction of Example 8 was concentrated in vacuo to give 122 mg of the title compound, which was identical to that prepared in Example 7. Unreacted title product of Example 5 was recovered in later fractions.

EXAMPLE 10

Methyl 11α,15S-bis[(triethylsilyl)oxy]-6,9α-epoxy-5S-fluoro-prosta-6,13E-dien-1-oate, Method A

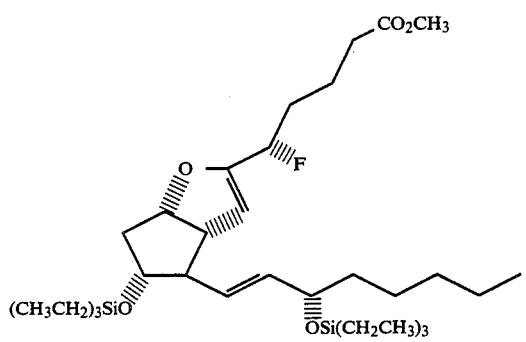

The title compound (495 mg) was prepared by the method of Example 6 using 655 mg of the title product of Example 2 instead of the title product of Example 4. The chromatography by Procedure 1 used 3% rather than 2% ethyl acetate.

$^{13}$C nmr (CDCl$_3$ containing trace of C$_5$D$_5$N): δ (ppm) 20.5 ($J_{CCCF}$=4 Hz, 3-C); 32.2 ($J_{CCF}$=25 Hz, 4-C); 87.9 ($J_{CF}$=169 Hz, 5-C); 154.3 ($J_{CCF}$=22 Hz, 6-C); 102.0 ($J_{CCCF}$=6 Hz, 7-C); 50.7 (8-C); 83.8 (9-C) tlc: R$_f$ 0.34.

EXAMPLE 11

Methyl 11α,15S-bis[(triethylsilyl)oxy]-6-9α-epoxy-5S-fluoro-prosta-5,13E-dien-1-oate, Method B The title compound (110 mg) was prepared by the method of Example 6, except that the title product of Example 3 (230 mg) was used instead of the title product of Example 4 and the mixture was heated at reflux for twenty hours. The chromatography by Procedure 1 used 3% rather than 2% ethyl acetate. The title compound was identical to that of Example 10.

EXAMPLE 12

Methyl 11α,15S-bis[[(1,1-dimethylethyl)diphenylsilyl]oxy]-6,9α-epoxyprosta-5Z,13E-dien-1-oate

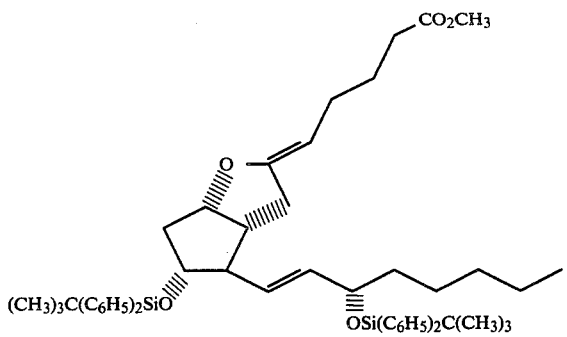

The title compound (6.8 g) was prepared by the method of Example 1 using 4.05 g of the methyl ester of prostaglandin F$_{2α}$, except for the following modifications: (1) The initial isomeric mixture of 5-iodoprostacyclins was not chromatographed before silylation and (2) silylation was effected with 7.0 ml of t-butylchlorodiphenylsilane rather than chlorotriethylsilane.

$^{13}$C nmr (CDCl$_3$ containing trace of C$_5$D$_5$N): δ (ppm) 51.4 (1-OCH$_3$); 174.5 (1-C); 33.6 (2-C); 24.8 (3-C); 25.6 (4-C); 95.1 (5-C); 155.1 (6-C); 33.5 (7-C); 44.1 (8-C); 83.7 (9-C); 41.5 (10-C); 78.3 (11-C); 54.0 (12-C); 73.8 (15-C); 37.9 (16-C); 24.6 (17-C); 31.8 (18-C); 22.5 (19-C); 14.0 (20-C) tlc: R$_f$ 0.29.

EXAMPLE 13

Methyl 11α,15S-bis[[(1,1-dimethylethyl)-diphenylsilyl]oxy]-6,9α-epoxy-5S-fluoro-6S-methoxyprost-13E-en-1-oate, Method A

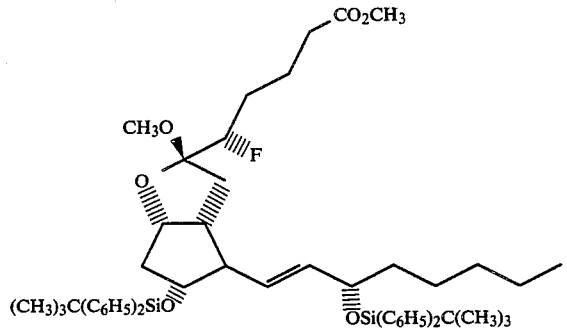

To a mixture of 9.09 g of the title product of Example 12 and 12.5 g of potassium carbonate in 300 ml of methanol, stirred at 25° under nitrogen, was added 4.5 ml of perchloryl fluoride over a one-hour period. During the addition the mixture slowly warmed to 32°. Volatiles were then evaporated under a slow nitrogen stream and the residue was taken up in a mixture of 500 ml of water and 500 ml of hexane. The organic layer was separated and then washed successively with water and brine, dried over sodium sulfate, filtered, and concentrated in vacuo. The residue was chromatographed by the method of Procedure 1 using gradient elution with 6 to 10% (by volume) of ethyl acetate, giving two major fractions. The flower fraction was concentrated in vacuo to give 2.19 g of the title compound.

nmr (CDCl$_3$ containing trace of C$_5$D$_5$N) Proton: δ (ppm) 3.14 (s, 3H, 6-OCH$_3$) $^{13}$C: δ (ppm) 29.7 (J$_{CCF}$=20 Hz, 4-C); 91.3 (J$_{CF}$=179 Hz, 5-C); 110.5 (J$_{CCF}$=23 Hz, 6-C); 36.7 (7-C); 44.4 (8-C); 81.4 (9-C) tlc: R$_f$0.11.

EXAMPLE 14

Methyl 11α,15S-bis[[(1,1-dimethylethyl)-diphenylsilyl]oxy]-6,9α-epoxy-5R-fluoro-6S-methoxyprost-13E-en-1-oate and Methyl 11α,15S-bis[[(1,1-dimethylethyl)-diphenylsilyl]oxy]-6,9α-epoxy-5R-fluoro-6R-methoxyprost-13E-en-1-oate, Method A

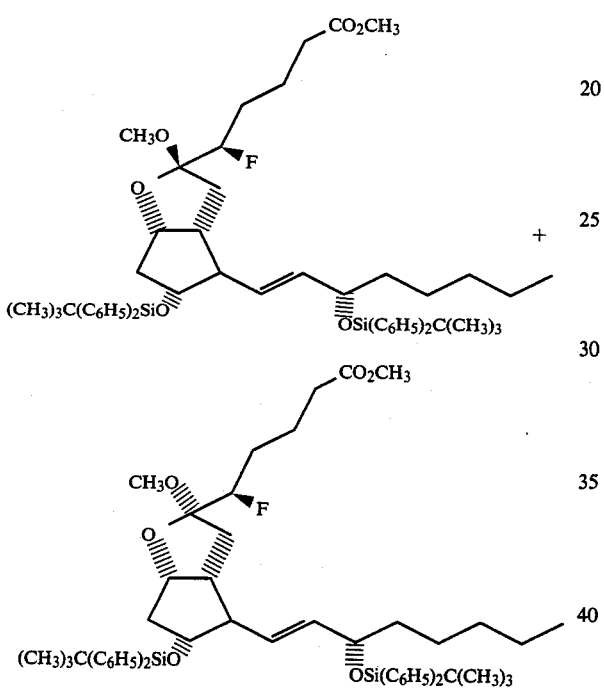

In addition to the title compounds, the poorly resolved faster chromatographic fraction of Example 13 contained the 5S,6R isomer, which was equilibrated to the more easily separated 5S,6S isomer (the title product of Example 13) by dissolving in methanol to which was then added 10 mg of camphorsulfonic acid. After the mixture was stirred for about eighteen hours, 0.5 ml of triethylamine was added and the mixture was concentrated under a slow nitrogen stream. The concentrate was diluted with 500 ml of diethyl ether containing a trace of triethylamine and then washed successively with 5% aqueous sodium dicarbonate and brine, dried over sodium sulfate, filtered, and again concentrated. The residue was again chromatographed as described in Example 13, giving three major fractions: (1) an initial impure fraction (1.77 g of material when concentrated); (2) a somewhat slower fraction containing 3.42 g of the title compounds as a mixture; and (3) a still slower fraction containing 0.69 g of the title product of Example 13. Repeating the chromatography of the initial impure fraction produced (1) nearly pure title 5R,6R isomer (0.43 g); (2) additional title compound mixture (2.03 g); and (3) additional title product of Example 13. Carbon-13 nmr indicated that the combined title compound mixture (5.45 g) consisted of about 90% of the 5R,6S isomer and 10% of the 5R,6R isomer.

Physical data for 5R,6S Isomer:

nmr (CDCl$_3$ containing trace of C$_5$D$_5$N) Proton: δ (ppm) 3.24 (s, 3H, 6-OCH$_3$) $^{13}$C: δ (ppm,) 29.8 (J$_{CCF}$=21 Hz, 4-C); 93.6 (J$_{CF}$=177 Hz, 5-C); 109.9 (J$_{CCF}$=21 Hz, 6-C); 39.3 (7-C); 44.8 (8-C); 82.3 (9-C) tlc: R$_f$0.19.

Physical data for 5R,6R Isomer:

nmr (CDCl$_3$ containing trace of C$_5$D$_5$N) Proton: δ (ppm) 3.24 (s, 3H, 6-OCH$_3$) $^{13}$C: δ (ppm) 29.6 (J$_{CCF}$=21 Hz, 4-C); 91.7 (J$_{CF}$=178 Hz, 5-C); 110.8 (J$_{CCF}$=22 Hz, 6-C); 34.1 (7-C); 44.4 (8-C); 82.2 (9-C) tlc: R$_f$0.20.

EXAMPLE 15

Methyl 11α,15S-bis[[(1,1-dimethylethyl)-diphenylsilyl]oxy]-6,9α-epoxy-5S-fluoro-6S-methoxyprost-13E-en-1-oate, Method B The title compound was prepared by the method of Example 13, except that cesium carbonate (which was soluble in the solvent used) was used instead of potassium carbonate and the reaction temperature was maintained at 15°.

Initial chromatography fractions contain small quantities of the 5-R-fluoro- and 5S-fluoro-6,13E-dienes.

EXAMPLE 16

Methyl 11α,15S-bis[[(1,1-dimethylethyl)-diphenylsilyl]oxy]-6,9α-epoxy-5R-fluoro-6S-methoxyprost-13E-en-1-oate and Methyl 11α,15S-bis[[(1,1-dimethylethyl)-diphenylsilyl]oxy]-6,9α-epoxy-5R-fluoro-6R-methoxyprost-13E-en-1-oate, Method B The title mixture was prepared by the method of Example 14 using the reaction mixture prepared in Example 15.

EXAMPLE 17

Methyl 11α,15S-bis[[(1,1-dimethylethyl)-diphenylsilyl]oxy]-6,9α-epoxy-5-fluoroprosta-5E,13E-dien-1-oate, Method A

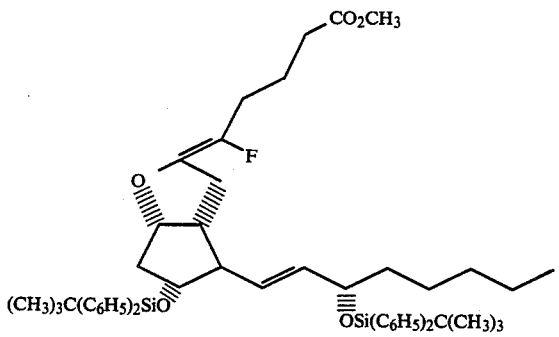

To a solution of 5.83 g of the title mixture of Example 14 (similarly for Example 16) in 50 ml of xylene and 1 ml of 2-picoline was added 10 mg of magnesium triflate. The mixture was stirred at reflux under nitrogen for four hours, then cooled and filtered. The filtrate was concentrated under a nitrogen stream and chromatographed by the method of Procedure 1 using gradient elution with 3 to 6% (by volume) of ethyl acetate, giving two major fractions. The faster fraction was concentrated in vacuo to give 403 mg of the title compound.

$^{13}$C nmr (CDCl$_3$ containing trace of C$_5$D$_5$N): δ (ppm) 26.9 (J$_{CCF}$=25 Hz, 4-C); 142.4 (J$_{CF}$=221 Hz, 5-C); 142.2 (J$_{CCF}$=48 Hz, 6-C); 30.2 (7-C); 44.6 (8-C); 84.5 (9-C) tlc: R$_f$0.28.

EXAMPLE 18

Methyl 11α,15S-bis[[(1,1-dimethylethyl)diphenylsilyl]oxy]-6,9α-epoxy-5R-fluoroprosta-6,13E-dien-1-oate, Method A

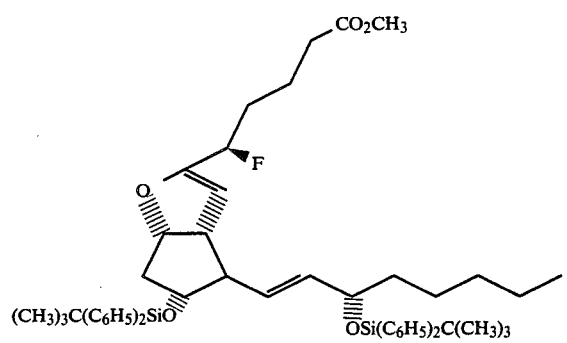

The slower chromatography fraction of Example 17 was concentrated in vacuo to give 4.66 g of the title compound.

$^{13}$C nmr (CDCl$_3$ containing trace of C$_5$D$_5$N): δ (ppm) 20.3 (J$_{CCCF}$=4 Hz, 3-C); 31.6 (J$_{CCF}$=22 Hz, 4-C); 87.2 (J$_{CF}$=168 Hz, 5-C); 153.5 (J$_{CCF}$=20 Hz, 6-C); 120.0 (J$_{CCCF}$=7 Hz, 7-C); 50.3 (8-C); 83.9 (9-C) tlc: R$_f$0.26.

Small quantities of unreacted title components of Example 14 were separately recovered in later fractions.

EXAMPLE 19

Methyl 11α,15S-bis[[(1,1-dimethylethyl)diphenylsilyl]oxy]-6,9α-epoxy-5E,13E-dien-1-oate, Method B A solution of 4.93 g of the title mixture of Example 14 (similarly for Example 16) in 10 ml of t-butylbenzene and 0.2 ml of 2-picoline was added through an air-cooled condenser to a refluxing mixture of 0.2 ml of 2-picoline and 5 mg of magnesium triflate in 40 ml of t-butylbenzene. The mixture was stirred at reflux under nitrogen for twelve minutes, then cooled and filtered. The filtrate was concentrated under a nitrogen stream and chromatographed as in Example 17, giving two major fractions, plus lesser quantities of the components of the starting mixture of Example 14. The faster fraction was concentrated in vacuo to give 388 mg of the title compound, identical to samples prepared by the method of Example 17.

EXAMPLE 20

Methyl 11α,15S-bis[[(1,1-dimethylethyl)-diphenylsilyl]oxy]-6,9α-epoxy-5R-fluoroprosta-6,13E-dien-1-oate, Method B The second major chromatography fraction of Example 19 was concentrated in vacuo to give 2.46 g of the title compound, identical to samples prepared by the method of Example 18.

Small quantities of unreacted title components of Example 14 were recovered separately in later fractions.

EXAMPLE 21

Methyl 11α,15S-bis[[(1,1-dimethylethyl)-diphenylsilyl]oxy]-6,9α-epoxy-5-fluoroprosta-5E,13E-dien-1-oate, Method C The title compound was prepared by the method of Example 19 using 0.47 g of the 5R,6R isomer (isolated in small quantities in Examples 14, 16, and 18), except that t-butyltoluene was used instead of t-butylbenzene. Chromatography by the method of Procedure 1 using 5% (by volume) of ethyl acetate gave three major fractions. The initial fraction was concentrated in vacuo to give 33 mg of the title compound, identical to samples prepared by the method of Example 17.

EXAMPLE 22

Methyl 11α,15S-bis[[(1,1-dimethylethyl)-diphenylsilyl]oxy]-6,9α-epoxy-5R-fluoroprosta-6,13E-dien-1-oate, Method C The second major chromatography fraction of Example 21 was concentrated in vacuo to give 143 mg of the title compound, identical to samples prepared by the method of Example 18.

Unreacted 5R,6R starting isomer of Example 14 was recovered in later fractions.

EXAMPLE 23

Methyl 11α,15S-bis[[(1,1-dimethylethyl)-diphenylsilyl]oxy]-6,9α-epoxy-5S-fluoroprosta-6,13E-dien-1-oate

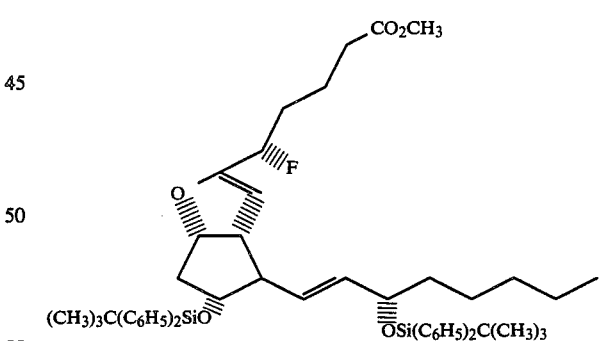

The title compound (334 mg) was prepared by the method of Example 6, except that the title product of Example 13 (388 mg) (similarly for Example 15) was used instead of the title product of Example 4 and the mixture was heated at reflux for ninety minutes. The chromatography by Procedure 1 used 5% rather than 2% ethyl acetate.

$^{13}$C nmr (CDCl$_3$ containing trace of C$_5$D$_5$N): δ (ppm) 20.3 (J$_{CCCF}$=4 Hz, 3-C); 31.6 (J$_{CCF}$=19 Hz, 4-C); 87.8 (J$_{CF}$=169 Hz, 5-C); 153.9 (J$_{CCF}$=22 Hz, 6-C); 101.8 (J$_{CCCF}$=6 Hz, 7-C); 50.6 (8-C); 83.3 (9-C) tlc: R$_f$0.26.

EXAMPLE 24

Mixture of methyl 11α,15S-bis[[(1,1-dimethylethyl)diphenylsilyl]oxy]-6,9α-epoxy-5R-fluoro-6S-methoxyprost-13E-en-1-oate and methyl 11α,15S-bis[[(1,1-dimethylethyl)-diphenylsilyl]oxy]-6,9α-epoxy-5R-fluoro-6R-methoxyprost-13E-en-1-oate by recycling methyl 11α,15S-bis[[(1,1-dimethylethyl)-diphenylsilyl]oxy]-6,9α-epoxy-5R-fluoroprosta-6,13E-dien-1-oate A solution of 0.45 g of the title product of Example 18 (similarly for Example 20 or 22) and 10 mg of pyridinium p-toluenesulfonate was stirred in 40 ml of methanol at room temperature. After three days, when no further change was observed by thin-layer chromatography (tlc, described in Procedure 3), the reaction was quenched with two drops of triethylamine. The mixture was concentrated to a small volume under a nitrogen stream, then dissolved in hexane. The solution was washed successively with 5% aqueous sodium bicarbonate and brine, dried over sodium sulfate, and concentrated to 0.44 g of the title mixture. Carbon-13 nmr indicated that the title mixture consisted of about 74% of the 5R,6S isomer and 26% of the 5R,6R isomer. No other component was indicated by tlc or nmr. The title mixture was subsequently used in reactions described in Example 17 through 22.

EXAMPLE 25

Removal of silyl protecting groups

Silylated compounds described in the preceding Examples were dissolved in tetrahydrofuran to which was added a slight molar excess of 1M tetrabutylammonium fluoride in tetrahydrofuran. The solutions were allowed to stand at room temperature until tlc (Procedure 3) indicated complete reaction had occurred; the triethylsilyl group required about fifteen minutes, whereas the t-butyldiphenylsilyl group required about twenty hours. The reaction mixtures were chromatographed by dry column liquid chromatography as described in Procedure 2. The following Examples 26 through 31 summarize the results.

EXAMPLE 26

Methyl 6,9α-epoxy-5-fluoro-11α,15S-dihydroxyprosta-5E,13E-dien-1-oate, Method A

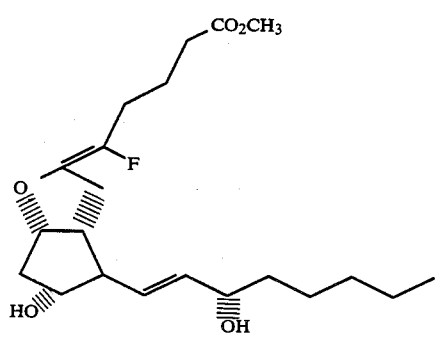

Using the method of Example 25, the reaction of 154 mg of the title product of Example 6 (similarly for Example 8) in 5 ml of tetrahydrofuran with 1 ml of 1M tetrabutylammonium fluoride for fifteen minutes afforded 67 mg of the title compound.

$^{13}$C nmr (CDCl$_3$ containing trace of C$_5$D$_5$N): δ(ppm) 26.7 (J$_{CCF}$=24.5 Hz, 4-C); 142.7 J$_{CF}$=224 Hz, 5-C); 141.6 (J$_{CCF}$=48 Hz, 6-C) tlc: R$_f$ 0.14

EXAMPLE 27

Methyl 6,9α-epoxy-5-fluoro-11α,15S-dihydroxyprosta-5E,13E-dien-1-oate, Method B

Using the method of Example 25, the reaction of 640 mg of the title product of Example 17 (similarly for Example 19 and 21) in 10 ml of tetrahydrofuran with 2 ml of 1M tetrabutylammonium fluoride for twenty hours afforded 279 mg of the title compound. The title compound was identical to samples prepared by the method of Example 26.

EXAMPLE 28

Methyl 6,9α-epoxy-5R-fluoro-11a,15S-dihydroxyprosta-6,13E-dien-1-oate, Method A

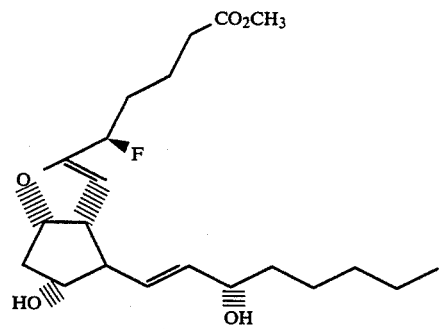

Using the method of Example 25, the reaction of 1.57 g of the title product of Example 7 (similarly for Example 9) in 10 ml of tetrahydrofuran with 5 ml of 1M tetrabutylammonium fluoride for fifteen minutes afforded 1.065 g of the title compound.

$^{13}$C nmr (CDCl$_3$ containing trace of C$_5$D$_5$N): δ(ppm) 20.3 (J$_{CCCF}$=3 Hz, 3-H); 32.0 (J$_{CCF}$=22 Hz, 4-C); 87.6 (J$_{CF}$=170 Hz, 5-C); 154.6 (J$_{CCF}$=22 Hz, 6-C); 101.5 (J$_{CCCF}$=6 Hz, 7-C); 51.1 (8-C); 83.5 (9-C) tlc: R$_f$ 0.17.

EXAMPLE 29

Methyl 6,9α-epoxy-5R-fluoro-11α,15S-dihydroxyprosta-6,13E-dien-1-oate, Method B

Using the method of Example 25, the reaction of the title product of Example 18 (similarly for Example 20 or 22) for twenty hours affords the title compound.

EXAMPLE 30

Methyl 6,9α-epoxy-5S-fluoro-11α,15S-dihydroxyprosta-6,13E-dien-1-oate, Method A

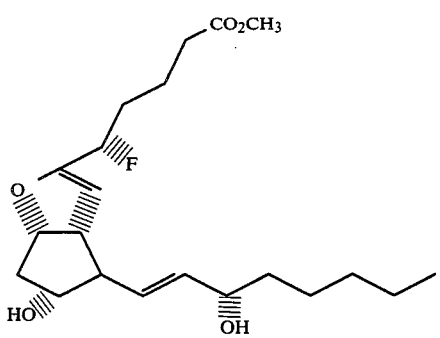

Using the method of Example 25, the reaction of 568 mg of the title product of Example 10 (similarly for Example 11) in 10 ml of tetrahydrofuran with 2 ml of 1M tetrabutylammonium fluoride for fifteen minutes afforded 325 mg of the title compound.

$^{13}$C nmr (CDCl$_3$ containing trace of C$_5$D$_5$N): δ(ppm) 20.3 ($J_{CCCF}$=5 Hz, 3-C); 31.9 ($J_{CCF}$=23 Hz, 4-C); 87.8 ($J_{CF}$=169 Hz, 5-C); 154.3 ($J_{CCF}$=22 Hz, 6-C); 101.9 ($J_{CCCF}$=6 Hz, 7-C); 50.9 (8-C); 83.3 (9-C) tlc: R$_f$0.17.

EXAMPLE 31

Methyl 6,9α-epoxy-5S-fluoro-11α,15S-dihydroxyprosta-6,13E-dien-1-oate, Method B

Using the method of Example 25, the reaction of 334 mg of the title product of Example 23 in 5 ml of tetrahydrofuran with 2 ml of 1M tetrabutylammonium fluoride for twenty hours afforded 147 mg of the title compound. The title compound was identical to samples prepared by the method of Example 30.

EXAMPLE 32

Saponification of methyl esters

The methyl esters described in the preceding Examples 26 through 31 were dissolved in a minimal amount of methanol (no more than about 1 ml of methanol for every 100 mg of ester) to which was then added with stirring a 5% molar excess of 1M aqueous sodium hydroxide. A total of about five to ten volumes of water was added in small portions, allowing any cloudiness to clear before adding another portion of water. The solutions were allowed to stir at room temperature. The reaction mixtures were concentrated to about half volume under a nitorgen stream, then freeze dried. The following Examples 33 through 35 summarize the results.

EXAMPLE 33

6,9α-epoxy-5-fluoro-11α,15S-dihydroxyprosta-5E,13E-dien-1-oic acid, sodium salt

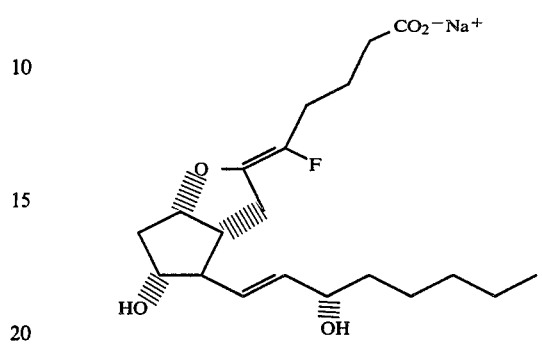

Using the method of Example 32, the reaction for twenty hours of 275 mg of the title product of Example 26 (similarly for Example 27) in 1 ml of methanol and 5 ml of water with 0.75 ml of 1M aqueous sodium hydroxide afforded 271 mg of the title compound.

$^{13}$C nmr (D$_2$O): δ(ppm) 27.8 ($J_{CCF}$=24 Hz, 4-C); 144.9 ($J_{CF}$=224 Hz, 5-C); 141.4 ($J_{CCF}$=49 Hz, 6-C).

EXAMPLE 34

6,9α-epoxy-5R-fluoro-11α,15S-dihydroxyprosta-6,13E-dien-1-oic acid, sodium salt

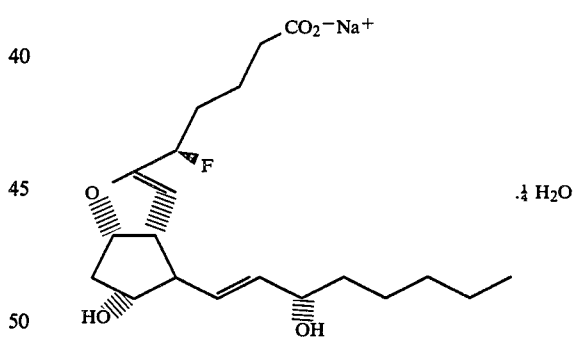

.¼ H$_2$O

Using the method of Example 32, the reaction for forty-two hours of 347 mg of the title product of Example 28 in 1 ml of methanol and 5 ml of water with 0.93 ml of 1M aqueous sodium hydroxide afforded 325 mg of the title compound.

$^{13}$C nmr (D$_2$O): δ(ppm) 22.0 ($J_{CCCF}$=4 Hz, 3-C); 32.7 ($J_{CCF}$=26 Hz, 4-C); 89.0 ($J_{CF}$=165 Hz, 5C); 154.6 ($J_{CCF}$=21 Hz, 6-C); 102.9 ($J_{CCCF}$=6 Hz, 7-C); 51.5 (8-C); 84.2 (9-C).

Elemental analysis. Calcd. for C$_{20}$H$_{30}$FO$_5$Na.¼H$_2$O: C, 60.52; H, 7.75.

Found: C, 60.66; H, 7.92.

EXAMPLE 35

6,9α-epoxy-5S-fluoro-11α,15S-dihydroxyprosta-6,13E-dien-1-oic acid, sodium salt

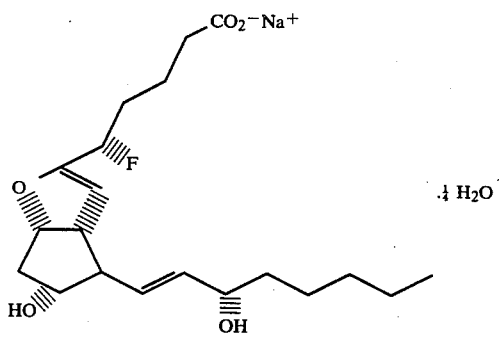

Using the method of Example 32, the reaction for twenty-eight hours of 264 mg of the title product of Example 30 (similarly for Example 31) in 1 ml of methanol and 5 ml of water with 0.72 ml of 1M aqueous sodium hydroxide afforded 263 mg of the title compound.

$^{13}C$ nmr ($D_2O$): δ(ppm) 22.2 ($J_{CCCF}$=6 Hz, 3-C); 32.7 ($J_{CCF}$=23 Hz, 4-C); 89.2 ($J_{CF}$=165 Hz, 5-C); 154.3 ($J_{CCF}$=19 Hz, 6-C); 103.8 ($J_{CCCF}$=7 Hz, 7-C); 50.9 (8-C); 83.3 (9-C).

Elemental analysis. Calcd. for $C_{20}H_{30}FO_5Na.\frac{1}{4}H_2O$: C, 60.52; H, 7.75.

Found: C, 60.69; H, 7.75.

What is claimed is:

1. A process for preparing 11α,15S-bis[(1,1-dimethylethyl)diphenylsilyloxy]-6,9α-epoxyprosta-5S-fluoro-6S-methoxy-13E-en-1-oate esters wherein
   (a) an 11α,15S-bis[1,1-dimethylethyl)diphenylsilyloxy]-6,9α-epoxyprosta-5S-fluoro-6R-methoxy-13E-en-1-oate ester is treated with a mild acid in methanol to give an 11α,15S-bis[(1,1-dimethylethyl)diphenylsilyloxy]-6,9α-epoxyprosta-5S-fluoro-6(R and S)-methoxy-13E-en-1-oate ester mixture, and
   (b) the resultant ester mixture is separated to give 11α,15S-bis[(1,1-dimethylethyl)diphenylsilyloxy]-6,9α-epoxyprosta-5S-fluoro-6S-methoxy-13E-en-1-oate ester.

2. A process according to claim 1 wherein the mild acid is camphorsulfonic acid.

3. A process according to claim 1 wherein the ester is the methyl ester.

4. A process according to claim 1 wherein the ester mixture is separated by chromatography.

5. A process according to claim 1 wherein
   (a) 11α,15S-bis[(1,1-dimethylethyl)diphenylsilyloxy]-6,9α-epoxyprosta-5S-fluoro-6R-methoxy-13E-en-1-oate methyl ester is treated with camphorsulfonic acid in methanol to give an 11α,15S-bis[(1,1-dimethylethyl)diphenylsilyloxy]6,9α-epoxyprosta-5S-fluoro-6(R and S)-methoxy-13E-en-1-oate methyl ester mixture, and
   (b) the resultant methyl ester mixture is separated by chromatography to give 11α,15S-bis[(1,1-dimethylethyl)diphenylsilyloxy]-6,9α-epoxyprosta-5S-fluoro-6S-methoxy-13E-en-1-oate methyl ester.

6. A process for preparing 11α,15S-bis[(1,1-dimethylethyl)diphenylsilyloxy]-6,9α-epoxyprosta-5R-fluoro-6,13E-dien-1-oate esters and 11α,15S-bis[(1,1-dimethylethyl)diphenylsilyloxy]-6,9α-epoxyprosta-5-fluoro-5E,13E-dien-1-oate esters wherein
   (a) an 11α,15S-bis[(1,1-dimethylethyl)diphenylsilyloxy]-6,9α-epoxyprosta-5R-fluoro-6,13E-dien-1-oate ester is treated with a mild acid in methanol,
   (b) the acidified solution is quenched with a base and concentrated,
   (c) the quenched mixture is extracted and concentrated to give an 11α,15S-bis[(1,1-dimethylethyl)diphenylsilyloxy]-6,9α-epoxyprosta-5R-fluoro-6(R and S)-methoxy-13E-en-1-oate ester mixture, and
   (d) the ester mixture is reacted with magnesium triflate and picoline to form 11α,15S-bis[(1,1-dimethylethyl)diphenylsilyloxy]-6,9α-epoxyprosta-5R-fluoro-6,13E-dien-1-oate and 11α,15S-bis[(1,1-dimethylethyl)diphenylsilyloxy]-6,9α-epoxyprosta-5-fluoro-5E,13E-dien-1-oate esters.

7. A process according to claim 6 wherein the mild acid is pyridinium p-toluenesulfonate.

8. A process according to claim 6 wherein the ester is the methyl ester.

9. A process according to claim 6 wherein
   (a) 11α,15S-bis[[(1,1-dimethylethyl)diphenylsilyl]oxy-6,9α-epoxyprosta-5R-fluoro-6,13E-dien-1-oate methyl ester is treated with a mild acid in methanol,
   (b) the acidified solution is quenched with a base and concentrated,
   (c) the quenched mixture is extracted and concentrated to give an 11α,15S-bis[[(1,1-dimethylethyl)diphenylsilyl]oxy]-6,9α-epoxyprosta-5R-fluoro-6(R and S)-methoxy-13E-en-1-oate methyl ester mixture, and
   (d) the ester mixture is reacted with magnesium triflate and picoline to form 11α,15S-bis[[(1,1-dimethylethyl)diphenylsilyl]oxy]-6,9α-epoxyprosta-5R-fluoro-6,13E-dien-1-oate methyl ester and 11α,15S-bis[[(1,1-dimethylethyl)diphenylsilyl]oxy]-6,9α-epoxyprosta-5-fluoro-5E,13E-dien-1-oate methyl ester.

* * * * *